United States Patent [19]

Hu et al.

[11] Patent Number: 5,510,622
[45] Date of Patent: Apr. 23, 1996

[54] X-RAY DETECTOR ARRAY WITH REDUCED EFFECTIVE PITCH

[75] Inventors: Hui Hu, Waukesha; Stanley Fox, Brookfield; Thomas L. Toth, Brookfield; Thaddeus Ulijasz, Brookfield; Armin H. Pfoh, New Berlin, all of Wis.

[73] Assignee: General Electric Company, Milwaukee, Wis.

[21] Appl. No.: 278,357

[22] Filed: Jul. 21, 1994

[51] Int. Cl.⁶ ............................................. G01T 1/161/1/20
[52] U.S. Cl. ................................................................ 250/367
[58] Field of Search ................................ 250/367; 378/19

[56] References Cited

U.S. PATENT DOCUMENTS 4,176,280  11/1979  Greschat et al. ...................... 378/19

FOREIGN PATENT DOCUMENTS 2-201288  8/1990  Japan ...................................... 250/367

*Primary Examiner*—Constantine Hannaher
*Attorney, Agent, or Firm*—Quarles & Brady

[57] ABSTRACT

Image artifacts are reduced in a volumetric CT scanner system by decreasing the detector pitch along one or both dimensions of a 2D detector array. Four different embodiments for reducing detector pitch without reducing the size of each detector element are disclosed.

5 Claims, 2 Drawing Sheets

X-RAY DETECTOR ARRAY WITH REDUCED EFFECTIVE PITCH

BACKGROUND OF THE INVENTION

The present invention relates to computed tomography (CT) imaging apparatus; and more particularly, to the construction of detector arrays for multislice and volumetric CT ("VCT") systems.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon a linear array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The x-ray source and detector array in a conventional third generation CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

A VCT scanner obtains in a single gantry rotation, 3D volume images that correspond to several conventional slice images. Several scanning approaches are used and they all employ a two-dimensional array of detector elements that gather attenuation measurements in the x, or "in-slice" direction and in the z, or "slice" direction. To reduce sampling aliasing artifacts in the reconstructed slice images, the resolution in both the slice and in-slice directions is maximized by reducing detector pitch. This is accomplished primarily by reducing the size of each detector element, but a limit is reached at which further resolution cannot be achieved because the active detector surface area becomes too small to produce an adequate signal. In other words, artifacts due to increased signal noise outweigh the reduction in image artifacts due to increased detector resolution.

SUMMARY OF THE INVENTION

The present invention relates to a two-dimensional array of detector elements in which individual detector elements in adjacent rows, or columns, or both rows and columns are altered to reduce the effective detector pitch along one or both dimensions of the detector array without reducing the surface area of the detector. Pitch is reduced along one dimension by translating alternate rows or columns of detector elements one-half the length of a detector element along that dimension. This may be accomplished with, but is not limited to either square or rectangular shaped detector elements. Pitch may also be reduced along one dimension by skewing the detector elements to effectively translate the centers of alternate rows or columns by one-half the length of the detector element along that dimension.

A general object of the invention is to reduce effective detector pitch along one of its dimensions without reducing the surface area of each detector element. By translating or skewing detector elements, the centers of detector elements in alternate rows or columns are offset by one-half the detector length along that dimension. By combining signals from the detector elements during image reconstruction, the effective pitch produced by the staggered detector centers is smaller than that of a conventional detector array.

Another object of the invention is to reduce effective detector pitch along both dimensions of a two-dimensional detector array without reducing the surface area of each detector element. By rotating square detector elements about their centers by 45°, the detector centers of adjacent rows and columns are staggered. By combining signals from the detector elements during image reconstruction, the effective pitch is smaller than that of a conventional detector array with the same detector elements.

A more specific object of the invention is to reduce effective detector pitch along one dimension of a two-dimensional detector array without increasing the difficulty of manufacture. Rather than translating alternate rows or columns of the detector array to stagger the detector centers, the shape of the detector elements can be skewed to accomplish the same result. The advantage of this approach is that the edges of the detector elements remain aligned in straight runs, which makes it easier to route conductive paths out of the detector array and makes it easier to construct collimator plates for positioning over the detector array to reject scatter.

DESCRIPTION OF THE PREFERRED EMBODIMENT

Figure 1:
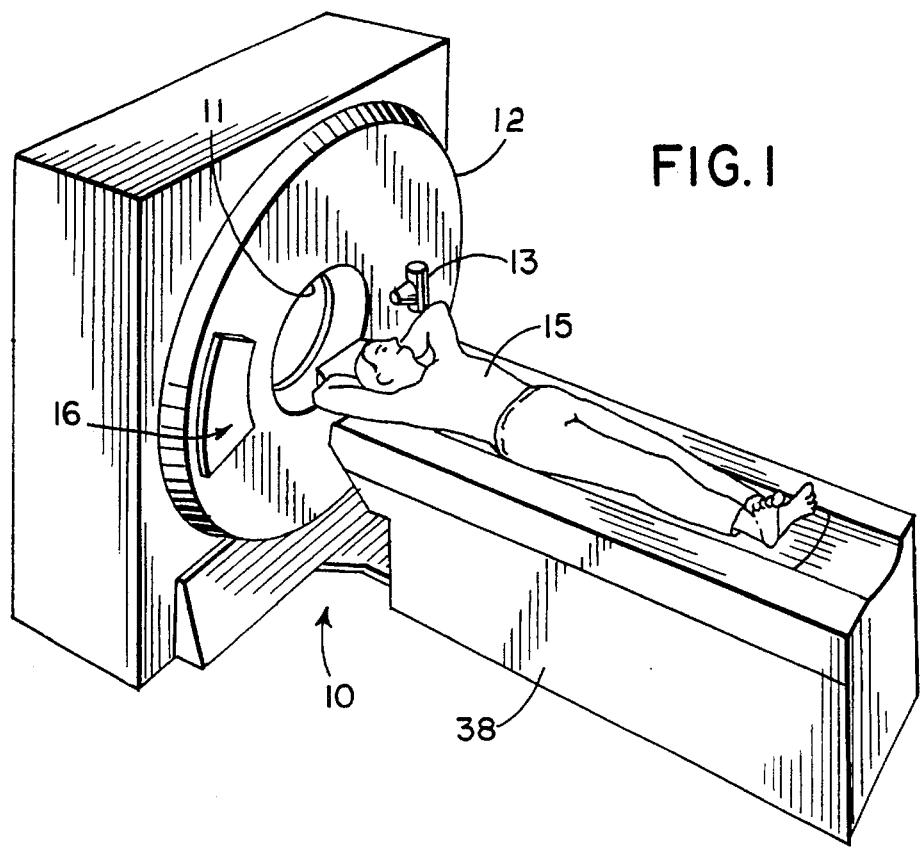
FIG. 1 is a pictorial view of a CT imaging system in which the present invention may be employed.
Figure 2:
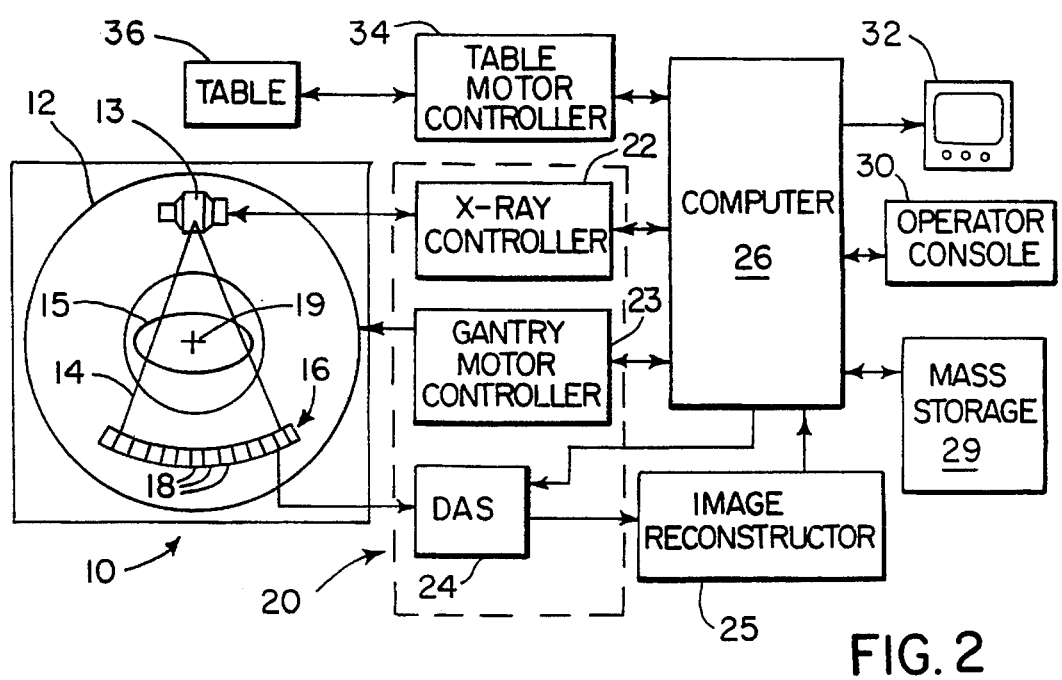
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantrymotor controller 23. In addition, computer 26 operates a table motor controller 34 which controls a motorized table 36 to position the patient 15 in the gantry 12.

Figure 4:
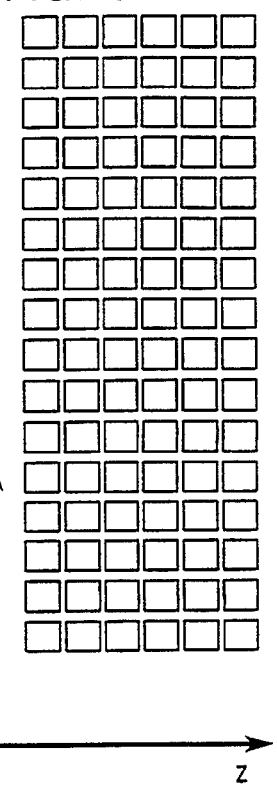
FIG. 4 is a plan view of a typical prior art detector array.

As shown in FIG. 4, a conventional two-dimensional detector array 16 is a matrix of square or rectangular shaped detector elements 18 arranged in columns which extend along the in-slice dimension (x-axis in the preferred embodiment) and rows which extend along the slice direction (z-axis in the preferred embodiment). The centers of the detector elements 18 are aligned in straight rows and columns and the resolution along the z-axis or the x-axis is measured by the distance between successive detector element centers.

Figure 3A:
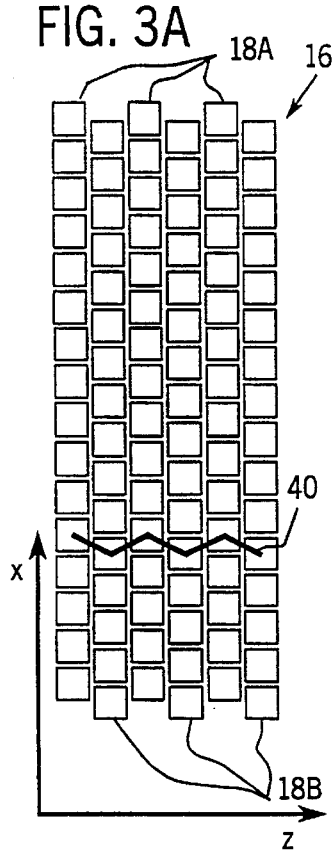
FIGS. 3A–3D are plan views of four preferred embodiments of the detector array which forms part of the CT imaging system of FIGS. 1 and 2.

Referring particularly to FIG. 3A, in a first embodiment of the invention detector pitch is effectively reduced along the x-axis by vertically translating alternate columns 18a and 18b of detector elements 18. The alternate columns 18a and 18b are translated by a distance equal to one-half the distance between detector element centers in the same column (i.e. the x-axis detector pitch). As a result, detector centers are staggered along the z axis as shown by the line 40. The effect of this staggering is to increase the number of sample points along the x axis and to effectively reduce detector pitch along that axis. A disadvantage, however, is that it increases the effective detector pitch along the z axis.

Figure 3B:
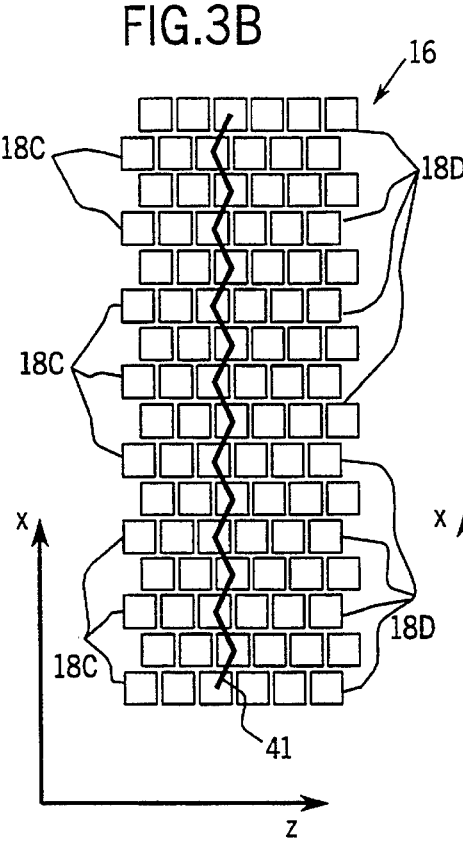

The same concept can be applied to reduce the effective detector pitch along the z axis. Referring particularly to FIG. 3B, in this embodiment alternate rows 18c and 18d are translated with respect to each other by one-half the z axis detector pitch. Consequently, the detector centers are staggered along the x axis as indicated by the line 41. the effect of this staggering is to increase the number of sample points along the z axis and to effectively reduce the detector pitch along that axis. A disadvantage is that it increases the effective detector pitch along the x axis.

Figure 3C:
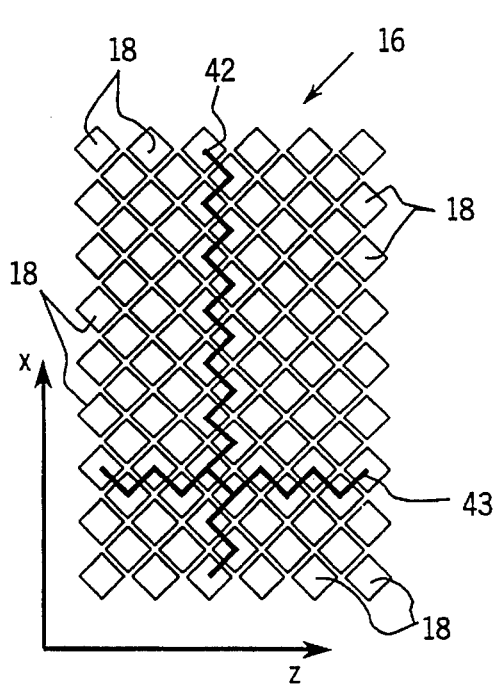

Referring particularly to FIG. 3C, in yet another embodiment of the invention detector pitch can be effectively reduced along both the x and z dimensions of the detector array 16. This is accomplished using, for example, square detector elements 18 which are rotated 45° about their centers. As a result, the centers of detectors 18 in adjacent columns are staggered as shown by line 42, and the centers of detectors 18 in adjacent rows are also staggered as shown by line 43. Consequently, the distance between centers of detector elements as measured along both the z and x axes are reduced to 0.707 the pitch of a corresponding prior art detector array using the same size detector elements. This is roughly a 30% reduction in the effective detector pitch along both the x and z dimensions of the two-dimensional detector array 16.

The manufacturability of a detector array 16 such as that shown in FIG. 3C is roughly the same as the prior art arrangement in FIG. 4. The edges of adjacent detector elements 18 are all aligned in straight lines. Such continuous detector element boundaries enables signal lines from each element 18 to be brought out to the edge of the array 16 along a straight path. In addition, if a collimator is to be mounted over the detector array 16 to reduce errors caused by x-ray scatter, it is easy to construct and align such a collimator along the straight boundaries between detector elements 18.

Figure 3D:
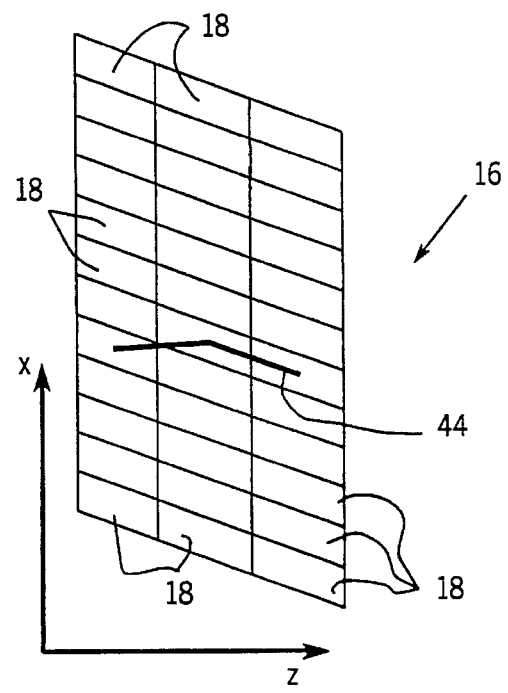

If these same manufacturing advantages are to be achieved, but a bigger reduction in detector pitch is required along only one detector dimension, the fourth embodiment of the invention shown in FIG. 3D is preferred. In this embodiment the adjacent detector element centers are staggered as shown by line 44, but this is accomplished by skewing the shape of the otherwise rectangular detector elements 18, rather than translating alternate columns. The result is a reduced effective pitch along the x axis as in the embodiment of FIG. 3A. However, the boundaries of adjacent detector elements 18 in this fourth embodiment are aligned in straight lines, making it easier to manufacture than the embodiment of FIG. 3A. It should be apparent to those skilled in the art that the detector elements 18 could also be skewed to stagger adjacent centers along the column direction if reduced pitch is required along the z axis rather than the x axis.

We claim:

1. A detector array for an x-ray volumetric CT system which produces a cone beam of x-rays, which comprises:

a plurality of quadrilateral-shaped detector elements arranged in a two-dimensional array to simultaneously sense the x-rays in the cone beam and produce corresponding electrical signals, with the centers of the detector elements aligned along a plurality of adjacent straight lines to form a corresponding plurality of columns, and with the detector elements in alternate columns being positioned such that their centers are staggered midway between the centers of detector elements in adjacent columns.

2. The detector array as recited in claim 1 in which the detector elements are rectangular-shaped and the alternate columns of detector elements are translated to stagger the centers of the detector elements therein.

3. A detector array for an x-ray volumetric CT system, which comprises:

plurality of quadrilateral-shaped detector elements arranged with their centers aligned along a plurality of adjacent straight lines to form a corresponding plurality of columns, and with the detector elements in alternate columns being positioned such that their centers are staggered midway between the centers of detector elements in adjacent columns;

in which the detector elements are square-shaped and their centers are also aligned along a plurality of adjacent straight lines to form a corresponding plurality of rows that are perpendicular to the columns.

4. A detector array for an x-ray volumetric CT system, which comprises:

a plurality of quadrilateral-shaped detector elements arranged with their centers aligned along a plurality of adjacent straight lines to form a corresponding plurality of columns, and with the detector elements in alternate columns being positioned such that their centers are staggered midway between the centers of detector elements in adjacent columns;

in which the detector elements are parallelogram-shaped and the centers of detector elements in alternate columns are staggered by skewing the detector elements.

5. The detector array as recited in claim 4 in which all boundaries that define the shape of each detector element in the detector array lie along one of a plurality of straight lines that extend to an edge of the detector array.

* * * * *